(12) United States Patent
Hutton et al.

(10) Patent No.: US 7,734,481 B1
(45) Date of Patent: Jun. 8, 2010

(54) COMPLIANCE AUDIT FOR INTEGRATED EMERGENCY MEDICAL TRANSPORTATION DATABASE SYSTEM

(75) Inventors: Kevin C. Hutton, Solana Beach, CA (US); Scott J. Jones, Escondido, CA (US)

(73) Assignee: Golden Hour Data Systems, Inc., San Diego, CA (US)

( * ) Notice: Subject to any disclaimer, the term of this patent is extended or adjusted under 35 U.S.C. 154(b) by 1725 days.

(21) Appl. No.: 10/007,641

(22) Filed: Nov. 6, 2001

Related U.S. Application Data (60) Provisional application No. 60/246,308, filed on Nov. 6, 2000.

(51) Int. Cl.
  *A61B 5/00* (2006.01)
  *G06F 19/00* (2006.01)
(52) U.S. Cl. .................. 705/3; 705/2; 705/4; 711/103; 713/2; 345/629
(58) Field of Classification Search .................. 705/2–4; 711/103; 713/2; 345/629
  See application file for complete search history.

(56) References Cited

U.S. PATENT DOCUMENTS

| | | | |
|---|---|---|---|
| 1,873,126 | A | 8/1932 | Hugershoff |
| 2,977,177 | A | 3/1961 | McLaughlin et al. |
| 3,921,318 | A | 11/1975 | Calavetta |
| 4,221,404 | A | 9/1980 | Shuffstall |
| 4,236,332 | A | 12/1980 | Domo |
| 4,814,711 | A | 3/1989 | Olsen et al. |
| 4,819,053 | A | 4/1989 | Halavais |
| 4,858,121 | A | 8/1989 | Barber et al. |
| 5,122,959 | A | 6/1992 | Nathanson et al. |
| 5,146,439 | A | 9/1992 | Jachmann et al. |

(Continued)

FOREIGN PATENT DOCUMENTS

JP    01319861 A    12/1989

(Continued)

OTHER PUBLICATIONS

Schriewer, "Airborne Ambulance Saves Precious Time," Tulsa World, May 22, 1996, pp. 1-2.

(Continued)

*Primary Examiner*—Gerald J. O'Connor
*Assistant Examiner*—Linh Le
(74) *Attorney, Agent, or Firm*—Manuel F. de la Cerra (57) ABSTRACT

An integrated medical database system for the emergency medical transportation business. In one aspect of the invention, the system includes a dispatch and demographic module, a clinical module, an administration module and a billing module. Each module may communicate data with one or more of the other modules to form a system incorporating data sharing, thus achieving an end-to-end automation of emergency medical care accounting. Internal consistency checks using specific libraries of modifiable data rules are performed by the system to ensure that proper treatments are performed according to a chosen diagnosis. The system includes a compliance audit module operating on data from the dispatch module and clinical module. The compliance audit module checks to ensure that data is consistent with high risk compliance areas. The results of the compliance audit module are forwarded to the billing module.

18 Claims, 4 Drawing Sheets

U.S. PATENT DOCUMENTS

| | | | |
|---|---|---|---|
| 5,283,829 A | | 2/1994 | Anderson |
| 5,327,341 A | | 7/1994 | Whalen et al. |
| 5,465,206 A | | 11/1995 | Hilt et al. |
| 5,483,443 A | | 1/1996 | Milstein et al. |
| 5,508,912 A | | 4/1996 | Schneiderman |
| 5,544,044 A | | 8/1996 | Leatherman |
| 5,550,976 A | | 8/1996 | Henderson et al. |
| 5,619,991 A | | 4/1997 | Sloane |
| 5,734,706 A | | 3/1998 | Windsor et al. |
| 5,761,278 A | | 6/1998 | Pickett et al. |
| 5,805,670 A | | 9/1998 | Pons et al. |
| 5,867,821 A | | 2/1999 | Ballantyne et al. |
| 5,874,897 A | | 2/1999 | Klempau et al. |
| 5,900,883 A | * | 5/1999 | Crucs .................. 345/629 |
| 5,911,132 A | | 6/1999 | Sloane |
| 5,940,013 A | | 8/1999 | Vladimir et al. |
| 5,974,355 A | | 10/1999 | Matsumoto et al. |
| 6,029,144 A | * | 2/2000 | Barrett et al. .................. 705/30 |
| 6,044,323 A | | 3/2000 | Yee et al. |
| 6,106,459 A | * | 8/2000 | Clawson .................. 600/300 |
| 6,117,073 A | | 9/2000 | Jones et al. |
| 6,151,581 A | | 11/2000 | Kraftson et al. |
| 6,324,516 B1 | * | 11/2001 | Shults et al. .................. 705/2 |
| 6,438,533 B1 | | 8/2002 | Spackman et al. |
| 6,529,876 B1 | | 3/2003 | Dart et al. |
| 6,542,905 B1 | | 4/2003 | Fogel et al. |
| 6,725,209 B1 | | 4/2004 | Iliff |
| 6,751,630 B1 | | 6/2004 | Franks et al. |
| 6,785,410 B2 | | 8/2004 | Vining et al. |
| 6,868,074 B1 | | 3/2005 | Hanson |
| 6,915,265 B1 | | 7/2005 | Johnson |
| 7,233,905 B1 | | 6/2007 | Hutton et al. |
| 2001/0034618 A1 | * | 10/2001 | Kessler et al. .................. 705/4 |
| 2002/0004729 A1 | * | 1/2002 | Zak et al. .................. 705/3 |
| 2002/0010679 A1 | | 1/2002 | Felsher |
| 2002/0065099 A1 | | 5/2002 | Bjorndahl |
| 2002/0120846 A1 | | 8/2002 | Stewart et al. |
| 2003/0036683 A1 | | 2/2003 | Kehr et al. |
| 2003/0093320 A1 | | 5/2003 | Sullivan |
| 2005/0240613 A1 | | 10/2005 | Logan |

FOREIGN PATENT DOCUMENTS

WO     WO 03102726     12/2003

OTHER PUBLICATIONS

Hudson, "Attorneys Fear Patient Transfer Claims in Malpractice Cases," Hospitals, Apr. 5, 1991, vol. 65, issue 7, pp. 44-48.

Segroves, "Navigation systems aids medical flights Bad weather landings are now possible at hospitals," News Sentinel, Aug. 7, 1994, pp. D7-8.

Spencer, Thomas, "Contracting for helicopter emergency transport services," Healthcare Financial Management, Aug. 1993, pp. 67-72.

www.aeromed-software.com, Feb. 5, 1998.

Public Law 104-191, Health Insurance Portability and Accountability Act of 1996, published Aug. 21, 1996, located at <http://aspe.hhs.gov/admnsimp/pl 104191.htm>.

Wyoming Medicaid Provider Manual Billing Manuals, Mar. 1, 1999. Section on HCFA 1500, chapters 4 (pp. 4-4, 4-7, and 4-54 in particular) and 9 (pp. 9-11 to 9-13). Section on Transportation, chapter 3 (3-12 to 3-22 in particular) and Appendices (C, D).

Obertots "Report on EMA Software Providers: Interfacing Modules; The Industry Standard" *ThinkThrough Tools, LLC*, Jul. 2007, 9 pages.

SweetTalk Newsletter, *Sweet Computer Services Inc.* vol. 2(3), Aug. 1993, 10 pages.

Various *Sweet Computer Services, Inc.'s* advertisements and brochures for SweetSoft™ software, 1990, 21 pages.

*Lancet Technology, Inc.* "Rescue One, The Complete EMS Database Management Solution" Brochure, 8 pages.

*Flightstar.* "A System Designed for Dispatchers, by Dispatchers" Flyer, 2 pages.

*Computing Technologies for Aviation, Inc.'s* Medical Air Transport System fact sheet, Sep. 1992, 2 pages.

*Droege Computing Services, Inc.* "Computing Services Emergency Flight System", Handout, 1 page.

*EMS Consultants Ltd.* "The Ultimate in EMS Software", Brochure, 30 pages.

EMS Expert @P-Docs Flyer, 2 pages.

*Westech System* brochure, 7 pages.

*LifeLink III* reports, printed Sep. 14, 1988, 14 pages.

*Arec Data Management Systems* Flyer, 3 pages.

*Iris* Product and Services Handout, 2 pages.

*DataWest's* Air-Ops Version 2.1 Software Manual, 15 pages.

*LiFlex* Computer Aided Dispatch System Flyer, 1991 or prior, 2 pages.

*UCS* Fire Rescue Incident Report, 1994, 10 pages.

*The Northern Virginia Sun* Article, dated May 10, 1993, 2 pages.

*Weekly Business* Article, dated Feb. 14, 1994, 1 page.

*UCS* The EMS Commander Brochure, 8 pages.

*Fireline* Brochure, printed Jul. 20, 2007, 4 pages.

*UCS* Pen Based Solutions for EMS Brochure, 4 pages.

*OuterLink* Web, 4 pages.

*AeroMed* Software Flight Management Module Version 2.2 Reference Manual, revised Nov. 10, 1992, 177 pages.

*AeroMed* Software Dispatch Module Version 2.2 Reference Manual, revised Nov. 10, 1992, 150 pages.

*EmsCharts, Inc.'s* Preliminary Invalidity Contentions, *Golden Hour Data Systems, Inc.* v *emsCharts, Inc. and Softtech,LLC*, U.S. District Court for the Eastern Division of Texas, Marshall Division, Civil Action No. 2:06-cv-381-TjW, Aug. 27, 2007, 22 pages.

\* cited by examiner

COMPLIANCE AUDIT FOR INTEGRATED EMERGENCY MEDICAL TRANSPORTATION DATABASE SYSTEM

RELATED APPLICATIONS

This application claims priority to U.S. Provisional Application No. 60/246,308, filed Nov. 6, 2000 and titled "INTEGRATED EMERGENCY MEDICAL TRANSPORTATION DATABASE SYSTEM WITH COMPLIANCE AUDIT," which is hereby incorporated by reference in its entirety. This application is related to U.S. application Ser. No. 10/007,644 entitled "DATA ACCURACY FILTER FOR INTEGRATED EMERGENCY MEDICAL TRANSPORTATION DATABASE SYSTEM," filed on Nov. 6, 2001, U.S. application Ser. No. 10/007,642 entitled "BILLING MODIFIER MODULE FOR INTEGRATED EMERGENCY MEDICAL TRANSPORTATION DATABASE SYSTEM," filed on Nov. 6, 2001, now issued as U.S. Pat. No. 7,233,905, and U.S. application Ser. No. 10/012,884 entitled "INTEGRATED EMERGENCY MEDICAL TRANSPORTATION DATABASE AND VIRTUAL PRIVATE NETWORK SYSTEM," filed on Nov. 6, 2001.

BACKGROUND OF THE INVENTION

1. Field of the Invention

This invention relates to an integrated medical database system. More specifically, this invention relates to a compliance filter for a medical database in the emergency medical transportation industry.

2. Description of the Related Technology

Current documentation procedures in the medical transport industry are based on an inefficient paper and pencil technology. Important information is frequently collected on loose sheets of paper. In the environment of emergency medical transport, little time is available to neatly chart and document all pertinent and required information on a single document. Dispatch data, demographic data and clinical data are normally tracked as fragmented pieces of information that are later coalesced into a complete patient chart. In many cases, these data include the same information, thus forcing the input of redundant information. The resultant chart is therefore vulnerable to being incomplete and unreliable. In a medical setting, incomplete information can lead to disastrous clinical results.

This same technology is used to support industry quality improvement and billing procedures and submit letters of transport justification. This paperwork is usually carried out well after the date the patient is encountered, prolonging account receivable times in many instances to the point of compromising and jeopardizing service compensation. Inventory stocking and tracking is similarly a victim of extended turnover times and is often incomplete and inaccurate.

The fragmentation throughout the medical transport environment is also evident in the myriad of entities throughout the country practicing different standards of care and documentation. As is the case in other segments of the healthcare industry, even seemingly simple tasks of communicating among the various entities, as well as among sections of a single providing entity, is severely hampered by the lack of a common communication format. This is especially evident when certain aspects of the system (such as computerized clinical laboratory result displays) have been upgraded with a uniquely tailored computerized system, while the remaining functions are still performed in an archaic manner. While the upgraded system may be effective for one singular aspect, such as dispatching, lab reporting, or chart dictating, the remainder of the system does not improve its effectiveness due to the other archaic components.

Current systems similarly depend on paper based systems that are labor and time intensive, and frequently suffer from human error, and forgetfulness. Compliance management is an absolute requirement in today's medical reimbursement environment, and there are significant financial penalties to not following a compliance management plan. What is desired is an electronic way of reducing the labor, time, and human error/forgetfulness. Furthermore, a capability where an adjustable percentage of clients are randomly and electronically audited and specific high-risk areas are identified for manual review would enhance such a medical system and are therefore also needed. An automated process is desired, such that before completion and transmission of data, the process would be initiated to assure data integrity, accuracy, and compliance with applicable reimbursement and regulatory standards. Such a process would identify discrepancies based on data collected from prior records and would allow immediate correction of inconsistent, inaccurate and non-compliant information.

SUMMARY OF CERTAIN INVENTIVE EMBODIMENTS

One aspect of the present invention is a computerized, integrated emergency medical transportation database system having a compliance audit component, the system comprising a medical emergency database configured to store at least clinical encounter information, patient demographic data and transport information; and a compliance audit component in communication with the medical emergency database, wherein the compliance audit component is configured to check to ensure that data in the medical emergency database for a current encounter is consistent with a high risk compliance area, and prompt for correction of the data where the data is not consistent.

Another aspect of the invention is a method of performing a compliance audit for an integrated emergency medical transportation database system, the method comprising collecting at least clinical encounter information, patient demographic data and transport information into a medical emergency database; identifying one or more high risk compliance areas; applying a specific library of modifiable data rules to ensure that the collected data is consistent with the high risk compliance areas; and prompting for correction of the data where the data is not consistent.

Yet another aspect of the invention is a computerized, integrated emergency medical transportation database system having a compliance filter, the system comprising a medical emergency database configured to store at least clinical encounter information, patient demographic data and transport information; and a compliance filter in communication with the medical emergency database, wherein the compliance filter is configured to use a specific library of modifiable data rules to ensure that data in the medical emergency database for a current encounter is consistent with a high risk compliance area, and prompt for correction of the data where the data is not consistent or compliant.

DETAILED DESCRIPTION OF THE CERTAIN INVENTIVE EMBODIMENTS

The following detailed description presents a description of certain specific embodiments of the present invention. In this description, reference is made to the drawings wherein like parts are designated with like numerals throughout.

For convenience, the discussion of the invention is organized into the following principal sections: Introduction, Hardware Overview, Data Flow Between Modules, Description of Software Module, and Conclusion.

INTRODUCTION

In certain embodiments, the present invention relates to an object oriented, interactive, international, client-server service for the medical transport industry. The service may integrate all aspects of patient record documentation into a single complete electronic chart. A server computer provides chart database information access to multiple transport providers simultaneously by securely transmitting, storing and maintaining standardized patient data, for instance, using guidelines set forth by the Scrambling Standards Organization. Individual transport-providing entities, such as helicopter and ambulance companies, obtain coded access to this server via phone lines with a modem equipped personal computer. Security is maintained by assigning each entity a unique code or identifier. Integrated Services Digital Network (ISDN) lines, Digital Satellite Systems (DSS), dedicated trunk lines (T1, T3, etc.), cable modem, DSL, or digital wireless systems may also be used for communication.

Each crew member involved in the patient's chart documentation, i.e. dispatcher, flight nurse, paramedic and physician, as well as administrator and collector, possess coded access to chart portions relevant to their responsibilities and level of care provided. The chart is then electronically generated from the compendium of the information entered in a standardized fashion and in accordance with minimum industry documentation requirements and the inventory of financial health care standards. The system provides complete and accurate chart documentation and maintains internal consistency between each separate module. Furthermore, any sentinel events are automatically referred to the appropriate, responsible party. A sentinel event is any action during the encounter that might require a further review. Examples of sentinel events are scene times exceeding 40 minutes, nonsensical or inconsistent data entry by an emergency transport crew member, supply shortages for equipment not utilized or repeated claim denials.

Billing can be submitted electronically to the appropriate party in an appropriate format that reduces the accounts receivable times for each patient encounter. Letters of justification are automatically generated as well as follow up letters and utilization review reports. Inventory reports and lists of necessary base supplies and medicines are also electronically updated to appropriate supply centers and administrators. Customized and research reports can also be provided rapidly.

Data security and an automatic backup are provided. Although the chart data is normally made the property of the respective transport service provider, the system can retain non-proprietary data to provide industry benchmarking, quality assurance analysis and clinical research opportunities. Such standardized data collection and documentation will furthermore enable the development of an Emergency Medical Services data library to assist in the justification and legislation of governmental preventive policies for public safety.

Hardware Overview

Figure 1:
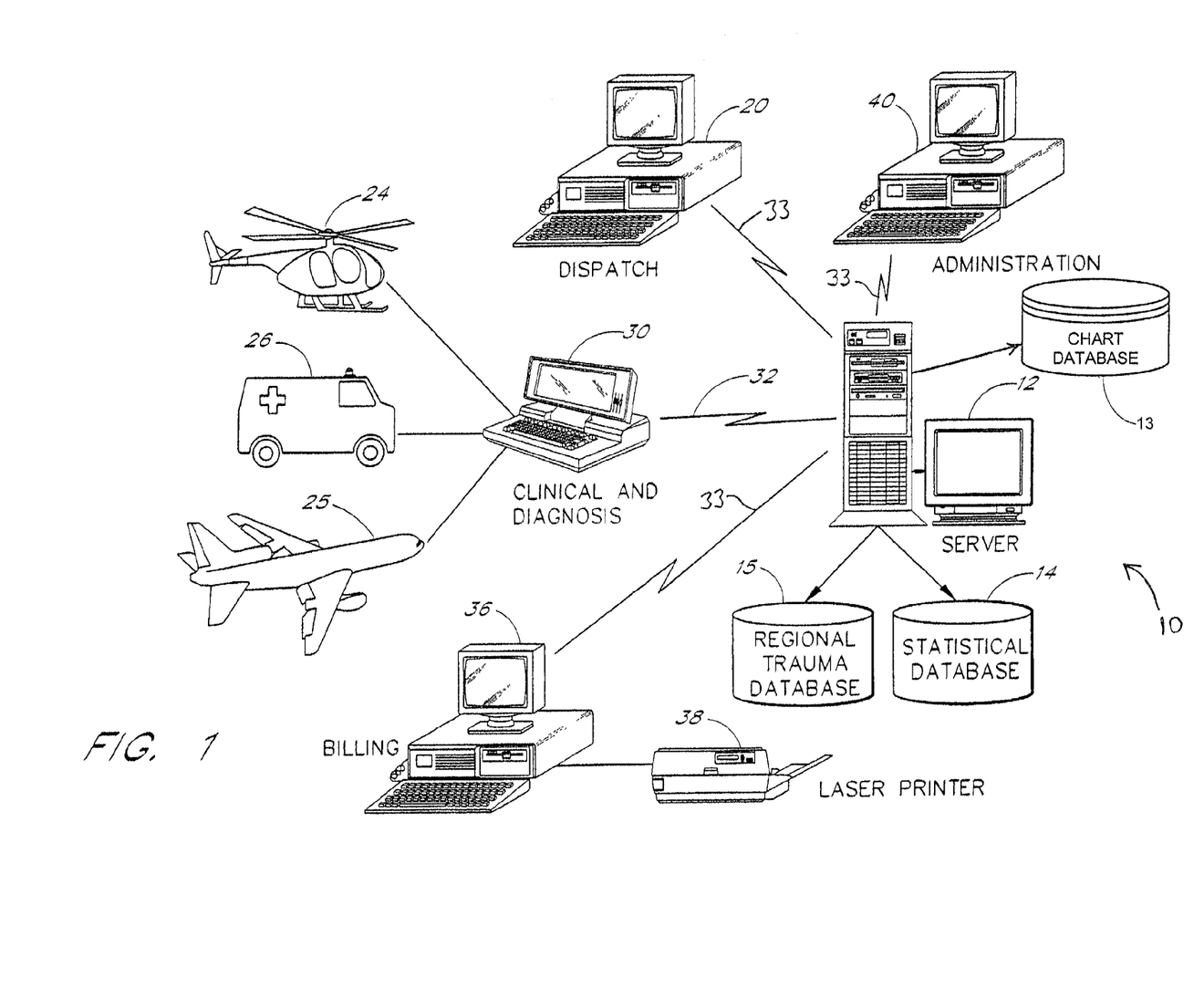
FIG. 1 is a diagram illustrating the on-line computing environment of one embodiment of the medical database system, including a dispatch interface computer, server computer, backup computer, clinical and diagnosis interface computer, administrative interface computer and billing interface computer.

FIG. 1 provides an overview of the computer hardware involved in one embodiment of the medical database system. In this embodiment, the medical database system 10 includes a server computer 12. The server computer 12 can be based on any well-known microprocessor such as those manufactured by Intel, Motorola, IBM or others. The server computer should be able to enable rapid simultaneous access to many users of the system. In one embodiment, the server computer 12 is an Intel Pentium III class computer having at least 256 Megabytes of RAM, a 10 gigabyte hard disk drive and a 500 MHz processing speed. Of course, many other standard or non-standard computers may support various embodiments of the medical database system 10.

The database application may be programmed in, for instance, ACIUS's 4th Dimension (4D) language and used in conjunction with the 4D Server and Client program. Also, another alternative computer environment is Microsoft Corporation's Visual Basic language with C++ middleware, and the BackOffice SQL Server program. It can therefore run in a standard Windows/Macintosh point-and-click office environment, and requires no additional, specialized software programming from the user. Of course, other standard or non-standard computer environments may support embodiments of the medical database system 10.

As illustrated, the server computer can access a chart database 13. The chart database 13 stores the previously described electronic charts corresponding to patients that have utilized emergency medical transportation. The server computer can also access a statistical database 14 to store and extract statistical information from data entered during patient encounters. The collected statistics might include, for example, average scene and transport times, number of transport requests per demographic region and time of year, average number of advanced procedures performed by crew members and number of complications encountered. In addition, the database 14 can hold information relating to the average length of time to process claims by category and payment plan.

The server computer can also be linked to a regional trauma database 15. The database 15 holds information relating to local trauma centers, emergency medical practice and other local trauma-related information.

The dispatch module on the server computer 12 can be accessed via an interface to a dispatch computer 20, which might reside, for example, at the dispatch center that receives the initial call to deploy an emergency medical team. The dispatch computer 20 can provide just a communications interface to the server computer 12 so that it acts as computer terminal, or it can contain a portion of the dispatch module.

Based on the scene location and needs of the patient, the dispatch center might deploy a helicopter 24, airplane 25, ambulance 26, or other transportation mechanism. The dispatch computer 20 communicates with software for collecting information on the patient encounter and scheduling and deploying a crew to assist the injured patient. Within the medical database system 10, the helicopter 24, airplane 25 or ambulance 26 would include a portable computer or computing device 30 (note that the portable computer 30 may be any electronic device that includes computing capability) that is used by the emergency medical team during the patient encounter. A wireless connection 32 can be made by the portable computer 30 to the server computer 12 to update the database 14 after any data has been entered. In other embodiments, other ways of communication with the server 12 can be used. The portable computer 30 can include clinical and diagnosis modules to assist the emergency medical team in treating the injured patient, or can act as a terminal to communicate with these modules on the server computer 12. As will be explained below, the clinical and diagnosis modules can help the emergency medical team determine the proper diagnosis and treatment of the patient.

The medical database system 10 also includes a billing computer 36 in communication with the server computer 12. The billing computer 36 interfaces with the server computer 12 to run the billing module for tracking charges. The software billing module can be stored directly on the billing computer 36 or, alternatively, stored on the server 12 and accessed via the billing computer 36. The billing module is used to track charges, inventory, and medical equipment. In addition, it is used during the patient encounter for providing billing functions within the medical database system 10. The billing computer 36 communicates with a laser printer 38 to provide printed reports and bills to hospitals, patients and medical centers.

An administration computer 40 interfaces with the server computer 12 to provide run administrative reports. These reports might relate to the statistical information contained in the statistical database 14. In addition, the administration computer 40 might run reports that relate to payroll, inventory, flight training or many other administrative issues.

It should be noted that the dispatch interface computer 20, portable computer 30, billing computer 36 and administration computer 40 can communicate with the server computer 12 through a variety of mechanisms, as shown by connection paths 32 and 33. For example, a wireless LAN or cellular network may connect each computer with one another. In another embodiment, dedicated or dial-up phone lines can be used to communicate between the different computers. Communication mechanisms may include networks such as the Internet and may include virtual private networks (VPNs).

Data Flow Between Modules

Figure 2:
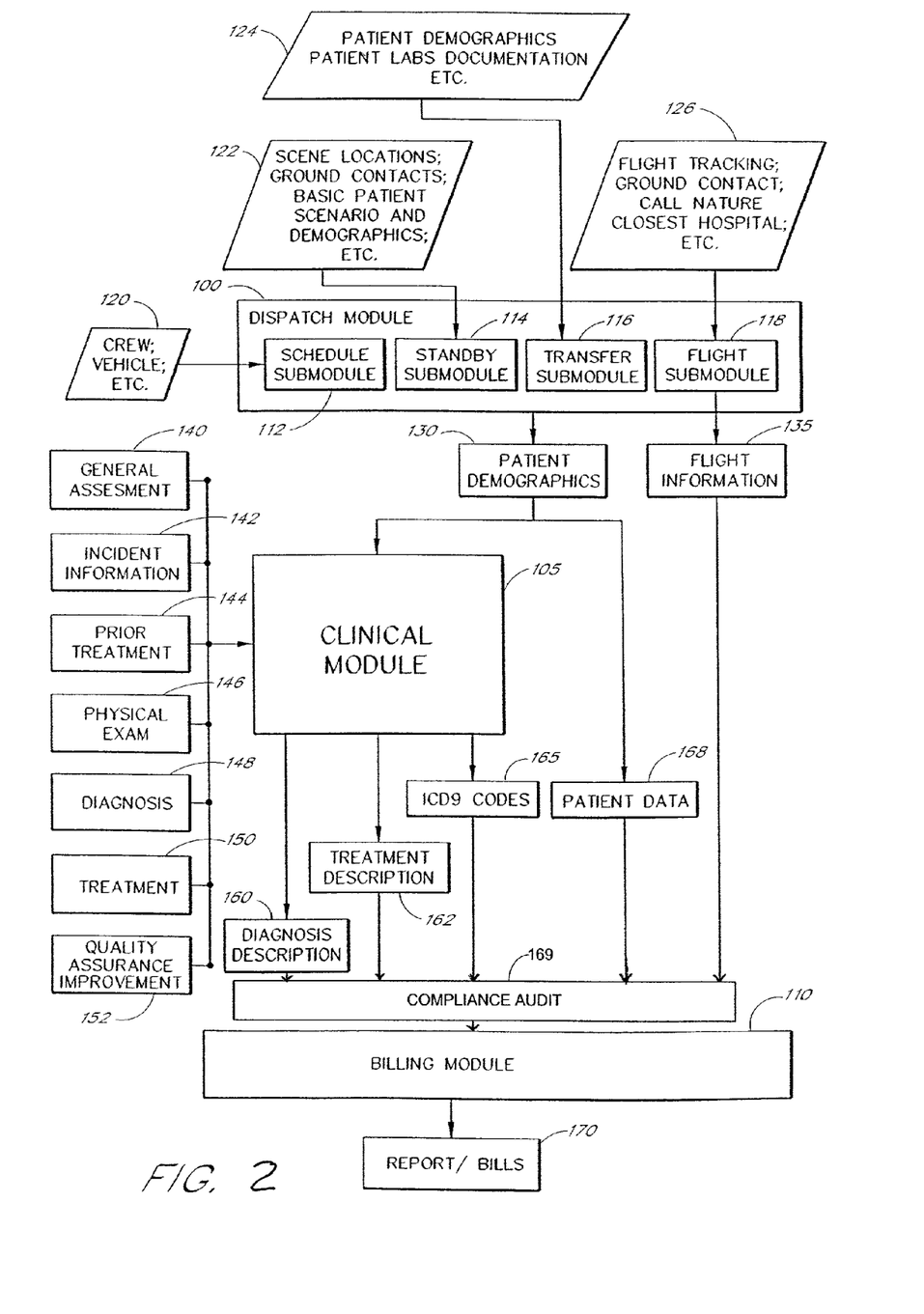
FIG. 2 is a block diagram illustrating one embodiment of the flow of data among a Dispatch module, a Clinical module, and a Billing module, in one embodiment of the medical database system.

Referring now to FIG. 2 (and also FIG. 1), a block diagram of one embodiment of the data flow between the various modules within the medical database system 10 is illustrated. FIG. 2 illustrates the flow of data between a dispatch and demographic module 100 (hereafter referred to as the dispatch module), a clinical module 105 and a billing module 110. The dispatch module 100 includes a scheduling submodule 112, a standby submodule 114, a transfer submodule 116 and a flight submodule 118. These various submodules process information received into the overall dispatch module 100. For example, crew information 120 is processed within the schedule submodule 112. In addition, scene information 122 is processed within the standby submodule 114.

Patient demographics and patient lab information 124 is processed within the transfer submodule 116. Flight tracking and other transportation information 126 is processed within the flight submodule 118. Once the various submodules within the dispatch module 100 have processed their respective information, a set of patient demographic information 130 and flight information 135 is made available to the remaining modules. For example, some of the patient demographic information 130 is imported into the clinical module 105.

In addition, many other pieces of data are placed within the clinical module 105. For example, the general assessment 140 of the patient that is taken by the emergency medical team is imported into the clinical module for further processing. In addition, other incident information 142 such as the type of incident (car accident, motorcycle accident, etc.) is sent to the clinical module 105. Prior treatment information 144 obtained from a physical exam of the patient or other information is also sent to the clinical module 105.

The prior treatment information might be important in determining whether the patient had already been treated for similar injuries thereby affecting the clinical diagnosis. Information collected from the physical exam 146 at the scene is also sent to the clinical module 105. In addition, any diagnosis 148 from the attending emergency medical team can be sent to the clinical module 105. It should be noted, as discussed below, that the medical database system 10 may also provide a diagnosis based on the physical exam information 146 and other information within the clinical module 105. This will be explained in more detail below.

Information relating to the treatment 150 of the patient is also sent to the clinical module 105. The medical database system 10 also includes a quality assurance database 152 which allows the emergency medical team to make suggestions or other comments that may be useful in additional treatments or incidents. For example, if the emergency medical team notes that a particular series of exam results has led to a unique diagnosis, this information can be input into the clinical module 105. Thus, the next time these same physical exam results are seen in a patient, the new diagnosis can be suggested to the emergency medical team.

Once the clinical module 105 has received its necessary information, data is output to a compliance audit module 169 and then further to the billing module 110. For example, a description of the diagnosis 160, a treatment description 162 or ICD-9 codes 165 can be sent from the clinical module 105 to the compliance audit module 169. As is well known, ICD-9 codes are a set of unique codes referring to most well-known medical procedures. These codes are used throughout the insurance industry to obtain payment for various medical procedures. In addition to the data from the clinical module 105, patient data 168 can be obtained from the patient demographic information 130. The patient data and demographic information 168 along with the flight information 135 are also processed by the compliance audit module 169. The compliance audit module 169 will be described in conjunction with FIG. 3 below. The output of the compliance audit module 169 can be fed into the billing module 110. This information is then used within the billing module 110 to generate reports and bills 170. As is to be expected, these reports and bills are sent to the various insurance companies and insurance providers. Thus, the medical database system 10 is an integrated system for providing many services within the medical industry. Further descriptions of the software modules are provided in Applicant's U.S. Pat. No. 6,117,073, which is hereby incorporated by reference.

Description of Software Module

The Compliance Audit Module

Figure 3A:
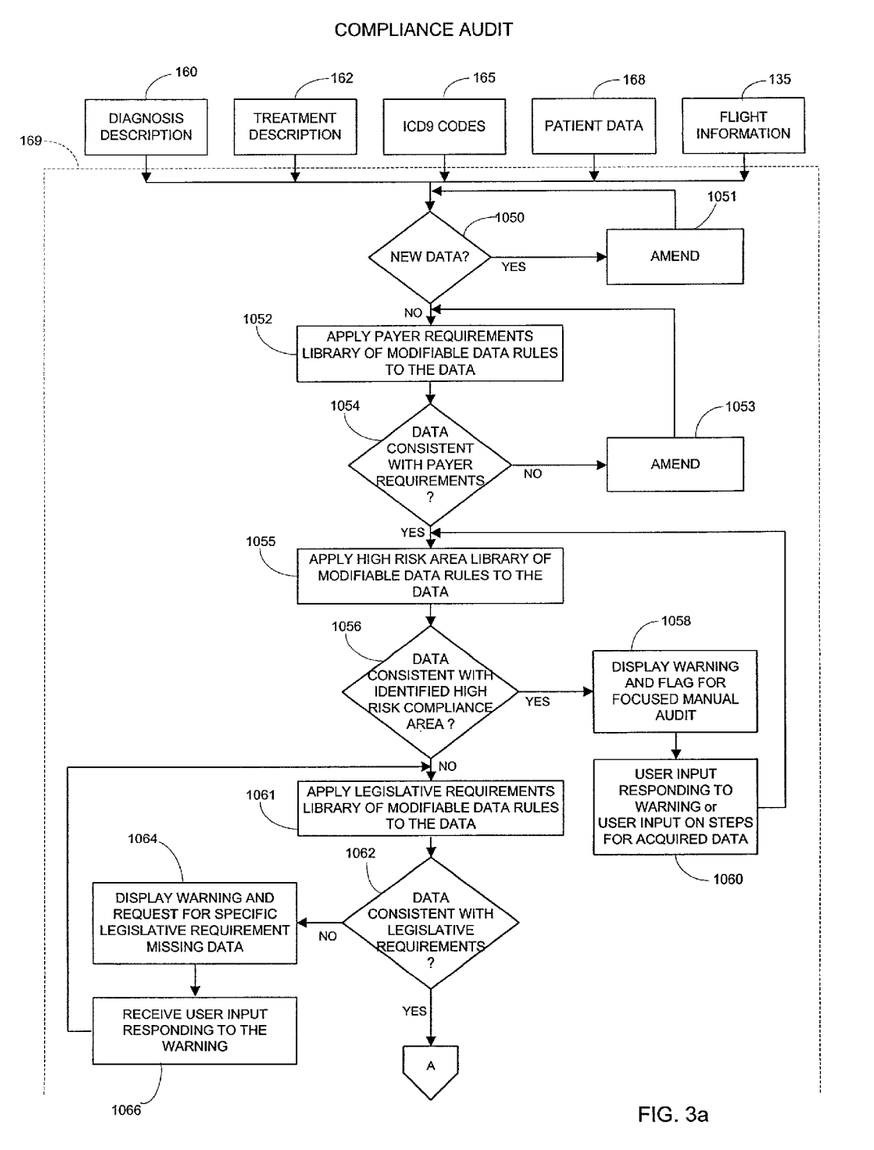
FIGS. 3a and 3b are a flowchart illustrating one embodiment of the Compliance Audit module process shown in FIG. 2.
Figure 3B:
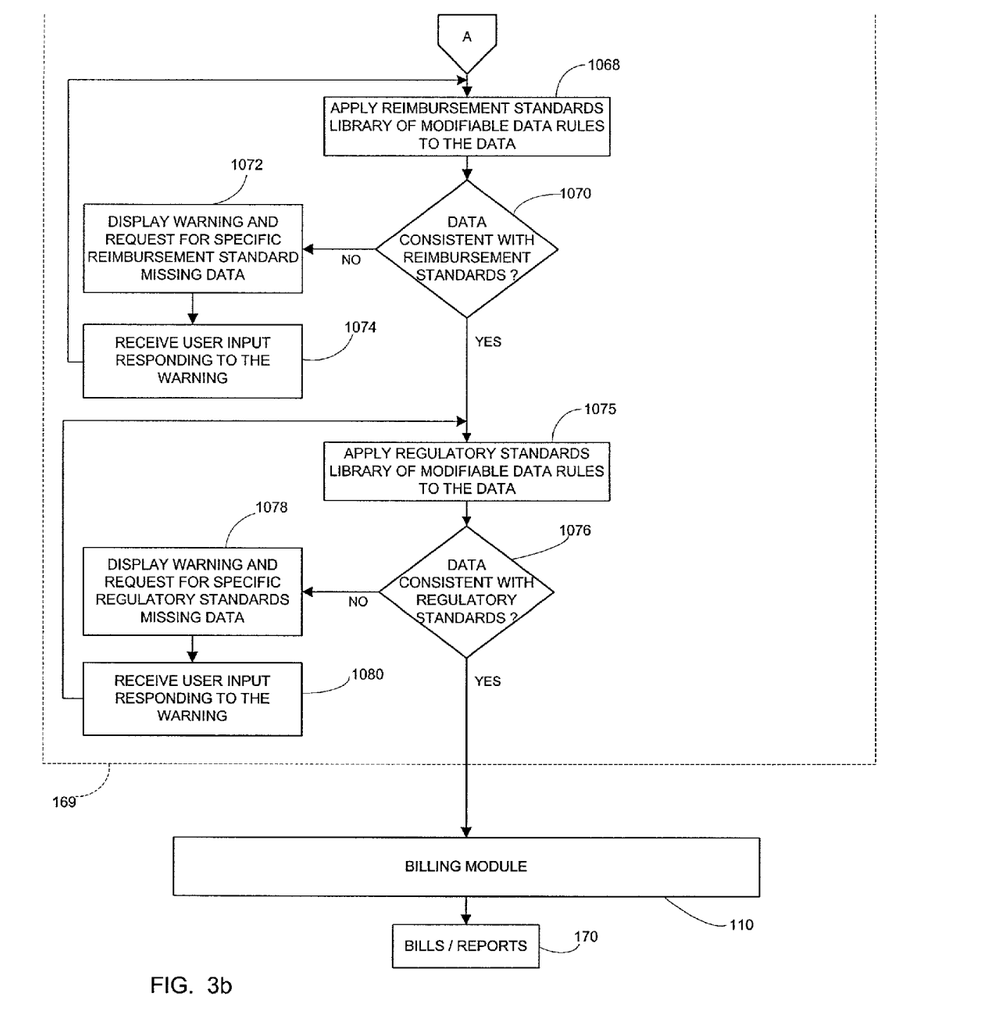

Referring now to FIGS. 3a and 3b, a flowchart illustrating one embodiment of the compliance audit module process 169 (FIG. 2) is described. The compliance audit module 169 may be configured for use as a compliance filter. In one embodiment, an adjustable percentage of clients are randomly and electronically audited and specific high-risk areas are identified for manual review. In another embodiment, before completion and transmission of data between modules and/or computers, the automated compliance audit 169 is initiated to assure data integrity, accuracy, and compliance with applicable reimbursement and regulatory standards. The compliance audit identifies discrepancies based on data collected from prior records and allows immediate correction of inconsistent, inaccurate and non-compliant information.

As described above, patient and demographic data and transport information is collected at the dispatch and demographic module 100. A diagnosis, with corresponding ICD-9 codes, and a treatment are developed at the clinical module 105.

The diagnosis description 160, the treatment description 162, the ICD-9 code(s) 165, the patient data 168, and the flight information 135 are forwarded to the compliance audit module process 169.

At decision state 1050, the received information 160, 162, 165, 168 and/or 135 is checked for new data. If the data is new, the compliance audit module process 169 proceeds to state 1051 where it is amended into the record, such as into the chart database 13. A further determination is then made at decision state 1050 for new data. If there is no new data, process 169 advances to state 1052 where a payer requirements library of modifiable data rules is applied to the data. At state 1052, an audit is performed to determine if the data is complete and consistent with payer compliance requirements. The data is compared to the library of modifiable data rules that correlate and filter the data to identify high risk areas. Process 169 proceeds to a decision state 1054 where the results of the audit (at state 1052) are checked to determine if the data is complete and consistent with payer compliance requirements. If the data is not complete or consistent, process 169 moves to state 1053 for amendment and reconsideration of the data, and then moves back to state 1052 to apply the library of modifiable rules again.

If the data is complete and consistent, process 169 advances to state 1055 where a high risk area library of modifiable data rules is applied to the data. Process 169 then moves to a decision state 1056 to determine whether the data is consistent with identified high risk compliance areas. A high-risk compliance area is a transport that meets specific criteria that are identified as carrying a risk for reimbursement fraud or abuse. An example of a high risk compliance area is for a two patient transport where the second patient is not medically necessary. An example of when the data may not be consistent is when the data may describe a stable patient with no injuries, but the crew may indicate that it is medically necessary. In one embodiment, the data is screened based on rules (at state 1055) for data points that identify the record as a high-risk compliance area. As an example, the dispatch and clinical data is screened and it is determined that the loaded mileage is less than ten miles and there are no extenuating circumstances documented that make this trip distance a justifiable transport by air. Medicare typically considers a transport of this distance as not medically necessary by air and will pay at ground rates. An exemplary rule can be as follows:

Does loaded mileage data indicate transport distance less than 10 loaded miles?
YES
Are acceptable extenuating circumstances documented?
NO
If answer above is No, then place display flight data in queue for manual review.

The process 169 identifies discrepancies based on data collected from prior records and allows immediately correction of inconsistent, inaccurate and non-compliant information. Thus, if it is determined at the decision state 1056 that the data is consistent with identified high risk compliance areas, process 169 moves to state 1058 where a warning and flag are set, in one embodiment, to indicate to the user that a manual review in either a focused or random audit should be performed. A warning is presented if the record indicates that additional user input is required to address identified compliance risk areas. The crew member completing the record is prompted/suggested to document their steps to minimize compliance risks at state 1060. For example, a circumstance that may provoke going to state 1058 is when new demographic data is acquired causing the record to be amended. At state 1060, there would be user input responding to the warning indicating that data would be entered. Alternatively, the user would detail what steps they took to acquire data so that others would not duplicate their work. It should be realized that the determination of whether the data is consistent with high risk compliance areas (at decision state 1056) includes a random sampling mechanism where random patient encounters that are within a high risk compliance group are selected for manual audit. At the completion of state 1060, process 169 moves back to state 1055 to apply the library of modifiable rules again. Thus, amended data from 1060 is tracked, reviewed, and formatted into the relevant data rules library.

If the data is consistent with identified high risk compliance areas, as determined at decision state 1056, process 169 then moves to state 1061 where a legislative requirements library of modifiable data rules is applied to the data. Process 169 proceeds to a decision state 1062 where the results are checked of screening the data using the specific data rules library (at state 1061) to determine whether the data is consistent with legislative requirements. At decision state 1062, the legislative requirements may relate to, for example, the transport of a patient to a facility that is not the closest capable facility. Other legislative requirements may relate to the personnel configurations required for patient transport, procedure practices or types of necessary documentation. For example, it may be required that at least one doctor, one nurse and one emergency medical technician (EMT) be sent on every call. If the data is not consistent with legislative requirements, as determined at decision state 1062, process 169 advances to state 1064 where the crew is warned and asked to amend specific missing data to meet legislative requirements. The user input responding to the warning is received at state 1066. At the completion of state 1066, process 169 then moves back to state 1061 to apply the library of modifiable rules again.

If the data is consistent with legislative requirements, as determined at decision state 1062, process 169 proceeds through an off-page connector A to state 1068 (on FIG. 3b) where a reimbursement standards library of modifiable data rules is applied to the data. Process 169 then advances to a decision state 1070 where the results are checked of the rules screening (at state 1068) to determine whether the data is consistent with reimbursement standards. An exemplary rule is as follows:

Is transport data entered consistent with the rules library for reimbursement standards?

If answer is NO

Display data that is not consistent and request adjudication/correction

Is new data consistent? if YES, move to next step

If NO, then place display transport in queue for manual review.

Present results of manual review for possible modification to data rules library.

The rules can be stored in rule libraries that are designed to be highly flexible to change as dictated by reimbursement, compliance, and regulatory changes.

If the data is not consistent with reimbursement standards, as determined at decision state 1070, process 169 advances to state 1072 where the crew is warned and asked to amend specific missing data to meet the reimbursement standards. The user input responding to the warning is received at state 1074. At the completion of state 1074, process 169 then moves back to state 1068 to apply the library of modifiable rules again. Thus, the user input is tracked, reviewed, and formatted into new data rules as applicable.

If the data is consistent with the reimbursement standards, as determined at decision state 1070, process 169 advances to state 1075 where a regulatory standards library of modifiable data rules is applied to the data. Process 169 then advances to a decision state 1076. At decision state 1076, the results of screening the data to determine whether the data is consistent with regulatory standards (at state 1075) are checked. If the data is not consistent with regulatory standards, as determined at decision state 1076, process 169 advances to state 1078 where the crew is warned and asked to amend specific missing data to meet the regulatory standards. The user input responding to the warning is received at state 1080. At the completion of state 1080, process 169 then moves back to state 1075 to apply the library of modifiable rules again. Thus, the user input is tracked, reviewed, and formatted into new data rules as applicable. In one embodiment, the acquired data may be screened against Consolidated Omnibus Reconciliation Act (COBRA) or Omnibus Reconciliation Act (OBRA) regulatory standards. This screening prevents the system from submitting a claim that does not satisfy these regulatory requirements.

For example, if a patient is transported from another hospital, the process 169 may search for the data point indicating that a signed Certificate of Medical Necessity accompanied the patient. If the Certificate of Medical Necessity data point is not found in the system, it may send a warning that in order for the accident costs to be reimbursed, the Certificate of Medical Necessity needs to be entered. Process 169 thus searches for compliance with the COBRA or OBRA rules, and the modifiable regulatory rules library and, if compliance is not found, notifies the user that more data is required. In another example, the patient might be left at the scene of an accident. If this occurs, the process 169 looks for appropriate documentation (based on the modifiable data rules library) of patient release against medical advice. If this data is not present, it flags this error and reports that such data is required for compliance with the COBRA and OBRA rules.

If the data is consistent with the regulatory standards, as determined at decision state 1076, process 169 completes and then the electronic chart record is released for billing review and bill preparation at the billing module 110.

CONCLUSION

Specific blocks, sections, devices, functions and modules may have been set forth. However, a skilled technologist will realize that there are many ways to partition the system of the present invention, and that there are many parts, components, modules or functions that may be substituted for those listed above.

As should be appreciated by a skilled technologist, the processes that are undergone by the above described software may be arbitrarily redistributed to other modules, or combined together in a single module, or made available in a shareable dynamic link library. The software may be written in any programming language such as C, C++, BASIC or Visual BASIC, Pascal, Java, and FORTRAN and executed under a well-known operating system, such as variants of Windows, Macintosh, Unix, Linux, VxWorks, or other operating system. C, C++, BASIC or Visual BASIC, Pascal, Java, and FORTRAN are industry standard programming languages for which many commercial compilers can be used to create executable code. A database programming language such as ACIUS's 4th Dimension (4D) language used in conjunction with the 4D Server and Client program may also be used.

While the invention has been described in connection with specific embodiments thereof, it will be understood that it is capable of further modification, and this application is intended to cover any variations, uses, or adaptations of the invention following, in general, the principles of the invention and including such departures from the present invention as would be understood to those in the art as equivalent and the scope and context of the present invention is to be interpreted as including such equivalents and construed in accordance with the claims appended hereto.

What is claimed is:

1. A computerized, integrated emergency medical transportation database system having a compliance audit component, the system comprising:

a medical emergency database configured to store at least clinical encounter data, patient demographic data and transport data, the clinical encounter data comprising the medical status of the patient and the transport data comprising the location of the clinical encounter, wherein at least a portion of the data is input by emergency medical personnel; and a compliance audit component in communication with the medical emergency database, wherein the compliance audit component is configured to:

check to ensure that data in the medical emergency database for a current encounter is consistent with a high risk compliance area, wherein checking to ensure consistency is based on data selected from the group consisting of the medical status of the patient, the location of the clinical encounter, and combinations thereof, and prompt the emergency medical personnel for correction of the data where the data is not consistent.

2. The system of claim 1, additionally comprising a billing module in communication with the medical emergency database, the billing module receiving data from the compliance audit component.

3. The system of claim 1, wherein the compliance audit component is additionally configured to record one or more attempts to obtain missing requirement data.

4. The system of claim 1, wherein the compliance audit component is additionally configured to apply a set of rules to determine whether the data for the current encounter is consistent with the high risk compliance area.

5. The system of claim 1, additionally comprising a dispatch and demographic module in communication with the medical emergency database, the dispatch and demographic module providing data to the compliance audit component.

6. The system of claim 5, wherein the dispatch and demographic module provides patient demographic data or transport data.

7. The system of claim 1, additionally comprising a clinical module in communication with the medical emergency database, the clinical module providing data to the compliance audit component.

8. The system of claim 7, wherein the clinical module provides a diagnosis description and a treatment description.

9. The system of claim 1, wherein the compliance audit component is configured to receive additional data from a user in response to the prompt for correction of the data.

10. The system of claim 9, wherein the additional data comprises information regarding the process of acquiring the data by a user.

11. The system of claim 2, wherein the billing module is configured to generate a bill based at least in part on the output of the compliance audit module.

12. The system of claim 11, wherein the billing module is configured to electronically submit the bill to a payor.

13. A method of performing a compliance check for an integrated emergency medical transportation database system, the method comprising:
    collecting at least clinical encounter data, patient demographic data and transport data into a medical emergency database, the data comprising the medical status of the patient and the transport data comprising the location of the clinical encounter, wherein at least a portion of the data is collected from a member of an emergency medical team;
    identifying one or more high risk compliance areas;
    applying a specific library of modifiable data rules to ensure that the collected data is consistent with the high risk compliance areas, wherein checking to ensure consistency is based on data selected from the group consisting of the medical status of the patient, the location of the clinical encounter, and combinations thereof; and
    prompting a member of the emergency medical team for correction of the data where the data is not consistent.

14. The method of claim 13, additionally comprising providing the corrected data to a billing module.

15. The method of claim 13, additionally comprising prompting for correction of the data where the data is not compliant.

16. The method of claim 13, additionally comprising generating a bill based at least in part on the corrected data.

17. The method of claim 13, additionally comprising submitting the bill to a payor.

18. A computerized, integrated emergency medical transportation database system having a compliance filter, the system comprising:
    a medical emergency database configured to store at least clinical encounter data, patient demographic data and transport data, the clinical encounter data comprising the medical status of the patient and the transport data comprising the location of the clinical encounter;
    a compliance filter in communication with the medical emergency database, wherein the compliance filter is configured to:
        use a specific library of modifiable data rules to ensure that data in the medical emergency database for a current encounter is consistent with a high risk compliance area, wherein checking to ensure consistency is based on data selected from the group consisting of the medical status of the patient, the location of the clinical encounter, and combinations thereof, and
        prompt for correction of the data where the data is not consistent; and
    a billing module in communication with the medical emergency database, the billing module receiving corrected data from the compliance filter, and the billing module being configured to generate a bill based at least in part on the corrected data.

* * * * *